(12) United States Patent
Jensen et al.

(10) Patent No.: US 6,309,500 B1
(45) Date of Patent: Oct. 30, 2001

(54) METHOD FOR MANUFACTURING CONTOURED AND LAMINATED MATERIALS

(76) Inventors: Robert Jensen, 646 Orangeburgh Rd., Rivervale, NJ (US) 07675; Jarl B. Jensen, 101 Getty St. Apt. LLV, Nyack, NY (US) 10960

(*) Notice: Subject to any disclaimer, the term of this patent is extended or adjusted under 35 U.S.C. 154(b) by 0 days.

(21) Appl. No.: 09/184,811

(22) Filed: Nov. 2, 1998

(51) Int. Cl.[7] .................................................... B32B 31/18
(52) U.S. Cl. ......................... 156/247; 156/238; 156/220; 156/269; 156/289; 156/324
(58) Field of Search .................................. 156/238, 247, 156/269, 289, 324, 199, 219, 220

(56) References Cited

U.S. PATENT DOCUMENTS

| | | |
|---|---|---|
| 1,988,787 | 1/1935 | Fowler . |
| 2,232,109 | 2/1941 | Gibbons . |
| 2,862,846 | 12/1958 | Blackford et al. . |
| 2,895,170 | 7/1959 | Carlile . |
| 2,988,774 | 6/1961 | Hely . |
| 3,327,708 | 6/1967 | Sokolowski . |
| 3,339,546 | 9/1967 | Chen . |
| 3,574,809 | 4/1971 | Fairbanks et al. . |
| 3,824,761 | 7/1974 | Wright . |
| 4,191,723 | 3/1980 | Vargiu et al. . |
| 4,323,533 | 4/1982 | Bramhall . |
| 4,340,557 | 7/1982 | Gross . |
| 4,357,935 | 11/1982 | Frantzich et al. . |
| 4,367,732 | 1/1983 | Poulsen et al. . |
| 4,369,284 | 1/1983 | Chen . |
| 4,414,970 | 11/1983 | Berry . |
| 4,538,603 | 9/1985 | Pawelchak et al. . |
| 4,551,490 | 11/1985 | Doyle et al. . |
| 4,556,441 | 12/1985 | Faassee, Jr. . |
| 4,693,858 | 9/1987 | Volke . |
| 4,762,124 | 8/1988 | Kerch et al. . |
| 4,867,748 | 9/1989 | Samuelson . |
| 4,867,821 | 9/1989 | Morgan . |
| 5,133,821 | 7/1992 | Jensen . |
| 5,508,334 | 4/1996 | Chen . |
| 5,520,762 | * 5/1996 | Rasmussen et al. ............. 156/289 X |
| 5,571,080 | 11/1996 | Jensen . |
| 5,716,475 | * 2/1998 | Botten et al. .................... 156/324 X |
| 5,935,363 | * 8/1999 | Gilman et al. ................... 156/269 X |

* cited by examiner

Primary Examiner—Curtis Mayes
(74) Attorney, Agent, or Firm—McDonnell Boehnen Hulbert & Berghoff

(57) ABSTRACT

A method for manufacturing end products such as wound dressings, surgical dressing, fixation wafers for prostheses, ostomy wafers, shoe inner-soles, and other laminated and contoured devices using a contouring and laminating station, a delaminating station, a driving station and a cutting station. A first outer layer having a backing film protected by a support layer is attached to a subject layer having predetermined malleable properties on one surface of the adhesive material. A second outer layer is attached on an opposing surface of the subject layer. As the layers are attached, the subject layer is contoured at the contouring and laminating station to produce a first intermediate product. The support layer is removed to produce a second intermediate product at a delaminating station. The second intermediate product is driven by the driving station to the cutting station to be cut into the end products.

12 Claims, 2 Drawing Sheets

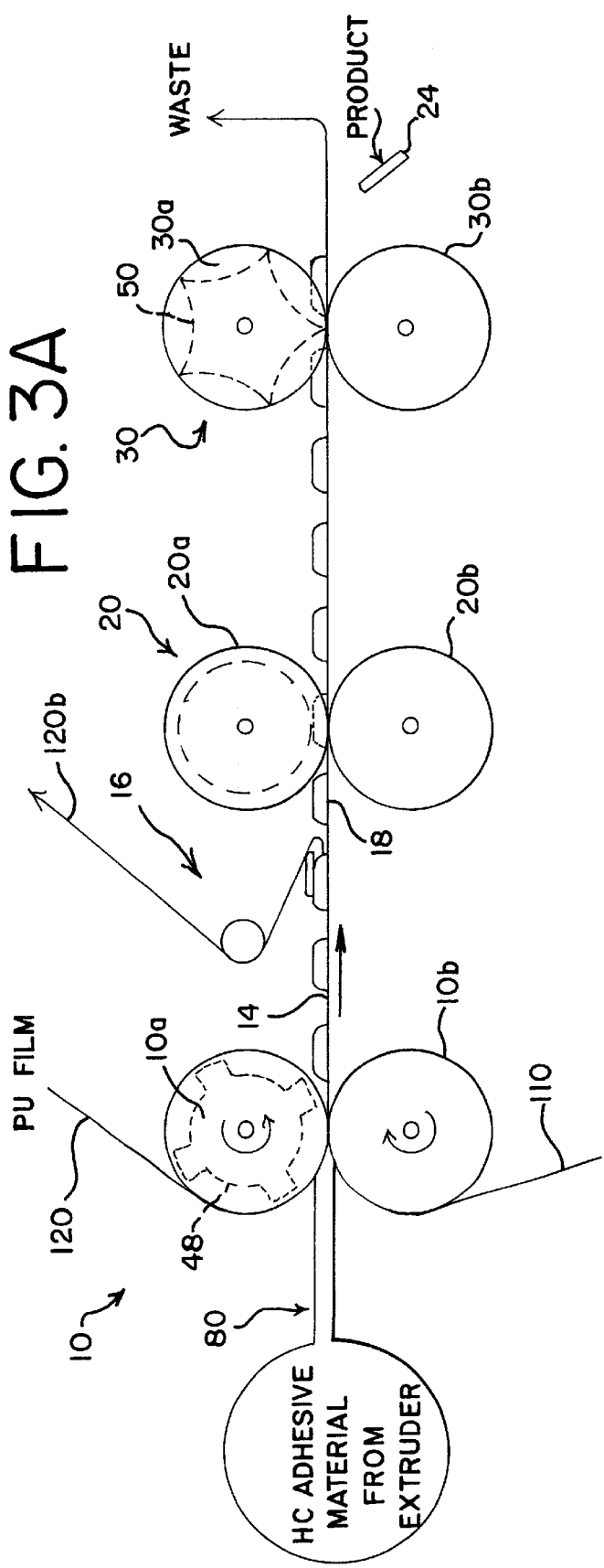

METHOD FOR MANUFACTURING CONTOURED AND LAMINATED MATERIALS

FIELD OF THE INVENTION

The present invention relates to the field of continuous line manufacturing, and more particularly to the field of manufacturing laminated and contoured components on a continuous manufacturing line.

DESCRIPTION OF RELATED ART

Laminated devices or components are available in many forms for a variety of purposes. Wound dressings, surgical dressings, medical adhesives and other like medical devices are often laminated to provide a skin-contacting layer, a backing layer and a release sheet layer.

The skin-contacting layer is used as a dressing or adhesive function and may be comprised of a variety of materials depending on the purpose of the device. Exemplary materials include hydrocolloid adhesives, hydrogels, non-wovens, foams, etc. It may be advantageous to contour, or shape the skin-contacting layer to provide conformability.

The backing layer is often attached to the skin-contacting layer to provide a protective covering. The release sheet layer is attached to the skin-contacting layer on the side opposite the backing layer with a release coating to permit removal of the release sheet layer during application. Each layer may be composed of other layers, or sub-layers depending on the application for which the device is intended. For example, the skin-contacting layer may have an adhesive layer attached to a moisture-absorbing or moisture-removing layer, such as a foam or non-woven.

Examples of wound dressings and methods for manufacturing such dressings are taught by Chen (U.S. Pat. No. 3,339,546) and Samuelson (U.S. Pat. No. 4,867,748, issued Sep. 19, 1989).

Other medical devices that may be laminated for purposes of application or packaging include fixation wafers for prostheses (e.g. breast prostheses) and ostomy wafers. Other devices that may be laminated and contoured include inner-soles for shoes. Instead of a skin-contacting layer such devices may include shock-absorbing materials, such as foam, soft rubber or other suitable materials. These materials may be covered by protective plastic films such as, polypropylene, polyethylene, polyurethane, etc.

Laminated devices may be difficult to manufacture. Because such devices may be high-volume devices, the method used for their manufacture should be as efficient as possible. Incremental costs may be magnified substantially as the volume of devices increases. In the case of medical devices, the need to manufacture in clean room or other specially controlled environment further complicates the process. Clean rooms may be expensive to maintain, particularly for high-grade medical devices that must be manufactured in clean rooms.

In addition, devices that are contoured may be more difficult to manufacture. Such contouring may involve shaping the materials comprising the devices at elevated temperature. The shaping may be performed using methods that stress the materials to a point at or near the ability of the materials to maintain a useful structure. For example, wound dressings may have backing layers made of polyethylene films that provide a flexible and impermeable covering for the skin-contacting layer. These materials may not have the strength to permit shaping at elevated temperatures.

One method for manufacturing wound dressings having skin-contacting layers made of hydrocolloid-adhesive and gel-like adhesive taught by Jensen in U.S. Pat. No. 5,133,821 (hereinafter Jensen '821) uses an in-line, substantially continuous process that minimizes the time and energy needed to make the dressings. Jensen '821 teaches a method in which the adhesive layer is covered by a protective layer on one surface and a release sheet layer on the opposing surface. The layers are contoured at a contouring station to produce a first laminate. The first laminate is carried through a delaminating station, which removes the protective layer to expose the surface of the adhesive. The exposed surface is then covered by a carrier layer at a laminating station and cut into discrete wound dressings at a cutting station.

The advantage of using the process in Jensen '821 is that the adhesive layer is protected by a protective layer during the contouring. The protective layer is made of paper or polyester that is coated with silicone for easy release during the removal of the layer. The backing layer is applied after the contouring of the adhesive layer such that the backing layer is not subject to the forces applied to the adhesive during contouring nor to the elevated temperatures that may be required to perform the contouring.

One problem with the methods taught in Jensen '821 is that the adhesive layer is exposed during the process. Because the laminating station adds the carrier layer to the exposed surface of the adhesive, or the layer to be contoured, the likelihood of introducing air pockets between the adhesive and the carrier layer is increased. It would be desirable to maintain the adhesive surface covered during the process.

The methods taught in Jensen '821 also include steps that add to the time required to manufacture the laminated and contoured devices. It would be further desirable to reduce the time to manufacture the laminated and contoured devices.

In addition, the laminating station may have the effect of deforming the contour achieved by the contouring station when the carrier layer is pressed to the exposed adhesive. It would be desirable to eliminate the need to apply too much pressure to the contoured adhesive surface.

The process in Jensen '821 yields substantial waste due to the removal of the protective layer prior to the addition of the backing layer. The cost of the waste is magnified when materials such as polyester are used. It would be desirable to reduce the cost of manufacturing laminated and contoured devices by eliminating the need to add and then remove a layer.

It would be further desirable to reduce the time required to carry out the process of manufacturing the laminated and contoured devices.

BRIEF DESCRIPTION OF THE DRAWINGS

Presently preferred embodiments of the invention are described below in conjunction with the appended drawing figures, wherein like reference numerals refer to like elements in the various FIGS., and wherein:

FIG. 3A shows a schematic diagram of one embodiment of the present invention.

FIG. 3B shows a cross section of a component used in the embodiment shown in FIG. 3A.

FIG. 4 shows a fragmentary cross-sectional view of an intermediate product of the method shown in FIG. 3A.

DETAILED DESCRIPTION OF THE PREFERRED EMBODIMENT

Figure 1:
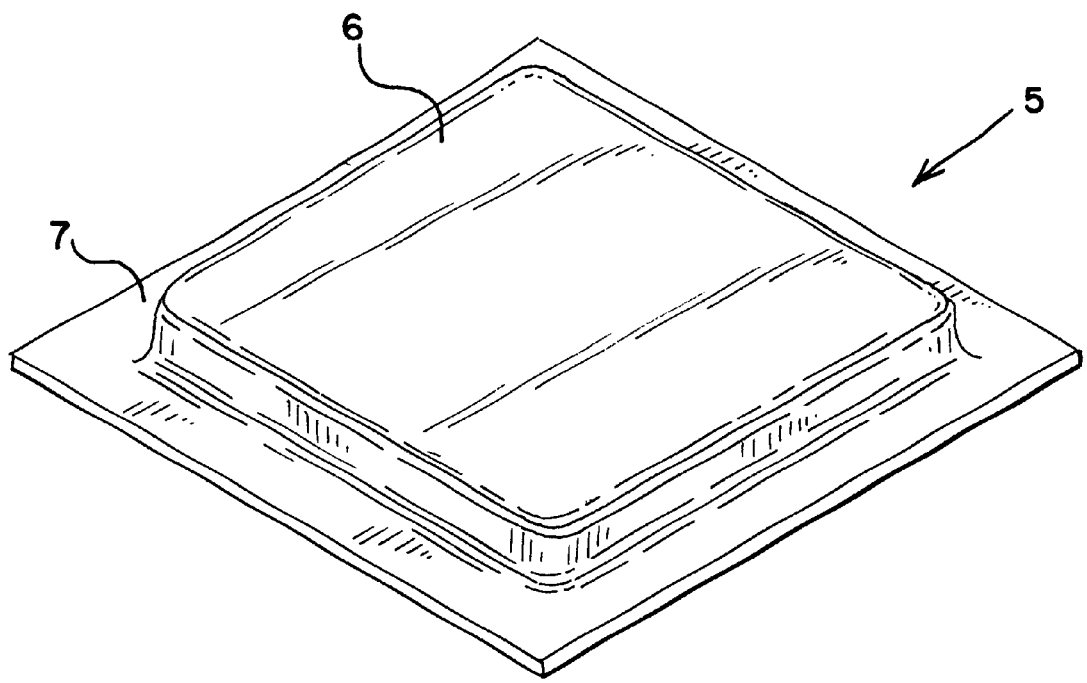
FIG. 1 represents a perspective view of one type of a laminated and contoured device that may be made by using the method of the present invention.

FIG. 1 shows an individual laminated and contoured device 24 that is representative of an end product that may be made by using methods according to the present invention. This device 5 has a thick portion 6 and a thin flange portion 7.

The device 5 may be a wound dressing, a surgical dressing, a fixation wafer for protheses, an ostomy wafer, or any medical device that is laminated and contoured. The device 5 may also include non-medical devices such as shoe inner-soles. The shape of the device 5 in FIG. 1 is rectangular, however, the device 5 may have any shape and contour.

Figure 2:
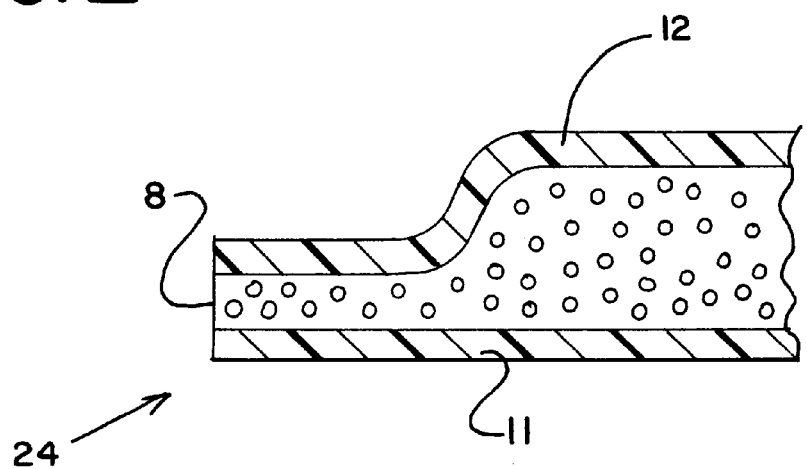
FIG. 2 represents a fragmentary cross-sectional view of the device in FIG. 1.

FIG. 2 shows a fragmentary cross-sectional view of one example of the end product 24 shown in FIG. 1. The end product 24 in FIG. 2 includes a subject layer 8, a first outer layer 12, and a second outer layer 11. The subject layer 8 may perform the primary function of the device. For example, for an inner-sole, the subject layer 8 may be a foam or other substance that provides the main cushioning of the inner-sole. For a wound dressing, the subject layer 8 may be a hydrocolloid-adhesive, a hydrogel, a polyurethane or other type of foam, a non-woven or any other suitable dressing material.

Preferred embodiments for a process for manufacturing laminated and contoured devices are described below where the end product 24 is a wound dressing having a hydrocolloid-adhesive as the subject layer 8. Those of ordinary skill in the art will appreciate that other laminated and contoured devices may be manufactured using embodiments of the present invention.

The first outer layer 12 provides a protective covering for the subject layer 8. A first outer layer 12 made of a polyethylene film, a polyurethane film, a non-woven or other suitable film may be used as a protective cover for the subject layer 8. Other materials may be used for the first outer layer 12 depending on the function of the subject layer 8.

The second outer layer 11 may be provided as a protective covering for the subject layer 8 on the side opposite the first outer layer 12. In a wound dressing, the second outer layer 11 may be a release sheet that may be removed during the application of the dressing. In a wound dressing, the second outer layer 11 is preferably made of a silicone release paper or other flexible material treated for easy removal from the subject layer 8. Other materials include polyester, polyurethane and polyethylene films.

Examples of the end product 24 used as a wound dressing as shown in FIG. 2 as well as of other types of products that may be manufactured using methods of the present invention may be found in U.S. Pat. No. 5,133,821 to Jensen (incorporated herein by reference); U.S. Pat. No. 5,591,447 to Jensen (incorporated herein by reference) and U.S. Pat. No. 4,867,748 to Samuelson.

Referring to FIG. 3A, the end product 24 shown in FIG. 2, where the first outer layer 12 is a backing film 120 for a wound dressing, the subject layer 8 is a hydrocolloid-adhesive 80 and the second outer layer 110 is a release sheet film, may be manufactured using a substantially continuous in-line method. The method shown in FIG. 3A includes steps of:

1. supplying the end product materials to a contouring and laminating station 10 to produce an intermediate product 14;
2. providing the intermediate product to a delaminating station 16 to produce a second intermediate product 18;
3. feeding the second intermediate product 18 to a driving station 20; and
4. cutting out the end products 24 using a cutting station 30.

At the contouring and laminating station 10, a substantially continuous backing film 120 is fed from a supply roller (not shown). The continuous film is fed into a contouring roller 10a and the release sheet film 110 is fed from a supply roller (not shown) at a second contouring roller 10b opposing the first contouring roller 10a. The hydrocolloid adhesive material is provided as a continuous strip at the contouring laminating rollers 10a, 10b.

The hydrocolloid adhesive material is preferably provided by extrusion such that the hydrocolloid adhesive material 80 is interposed between the backing layer film 120 and the release sheet film 110. The hydrocolloid adhesive material, or any other material selected for the subject layer 8, may also be ram-fed, pressed, injected or fed as a film.

The attached layers (i.e. the backing film 120, the adhesive layer 80 and the release sheet layer 110) are contoured by the co-operating rotational action of the contouring and laminating roller 10a and the second roller 10b. The contouring roller 10a has been relieved around its peripheral surface to provide shaped pockets 48. The pockets 48 are shaped according to the desired final contour of the end product 24.

A cross-sectional fragmentary view of the backing film 120 is shown in FIG. 3B. The backing film 120 includes a backing layer 120a and a support layer 120b. The support layer 120b protects the backing layer 120a during the contouring by the contouring roller 120a. As the laminate is contoured, the recess 48 in the roller 10a applies a force to the support layer 120b, the backing layer 120a and the adhesive layer 80 that combined with the malleability of the adhesive layer 80, stresses the backing film 120. The backing layer 120a is preferably made of a polyethylene film. By applying the backing film 120 with the support layer 120b, the backing film 120a is protected regardless of its thickness and material. The silicone release coating on the support layer 120b allows for easy later removal. One of ordinary skill in the art will appreciate that other backing films 120 may be used.

Referring back to FIG. 3A, the rotational action of the contouring roller 10a and the second roller 10b as the three layers are supplied between the rollers produces a laminated first intermediate product 14. A cross-sectional view of the intermediate product 14 is shown in FIG. 4. As shown in FIG. 4, the intermediate product 14 includes the support layer 120b and the backing layer 120a that comprise the backing film 120, the adhesive layer 80 and the release sheet film 110.

Referring back to FIG. 3A, the support layer 120b is removed at the delaminating station 16 to produce a second intermediate product 18. The second intermediate product 18 is carried through the driving rollers 20a and 20b at the driving station 20. The driving station 20 advantageously moves the continuous strip of first and second intermediate products to the cutting station 30, however, the driving station 20 is optional. The second intermediate product 18 includes the backing layer 120a, the adhesive layer 80 and the release sheet film 110. Another advantage of using the backing film 120 with the support layer 120b is that at the removal of the support layer 120b at the delaminating station 16 the adhesive layer 80 remains covered. The need for separate laminating station after the delaminating station 16 is precluded thereby providing a more efficient and less wasteful process.

The driving cylinder 20a is preferably coated with rubber and driven to rotate to carry the second intermediate product 18 to the cutting station 30. At the cutting station 30, a cutting roller 30a and the second cutting roller 30b are rotated at a selected speed to cut the second intermediate product 18 into individual wound dressings that make up the end product 24. The first cutting roller 30a comprises a cutting pattern shaped according to the shape selected for the end product 24. The end products 24 are delivered to a collection site or to a subsequent packaging operation.

The rollers the contouring and laminating station 10, the driving station 20 and the cutting station 30 are rotated in a timed and synchronized relationship to each other to provide the desired spacing and contours between the dressings. This timed relationship may be provided mechanically, electro-mechanically, electronically or by other suitable means. The individual stations should be individually adjustable with respect to the spacing between each pair of associated rollers to provide or compensate for the desired thickness of the wound dressing.

While examples of preferred embodiments of processes for manufacturing the end product 24 wound dressing have been described, it is to be understood by one of ordinary skill in the art that alternative embodiments falling within a scope of the claims are possible. For example, it may be possible to eliminate the driving station 20 leaving only the contouring and laminating station 10 and the cutting station 30. In addition, other stations may be added to provide additional features and advantages.

The methods of manufacturing the end product 24 described above with reference to FIG. 3A may also be used to manufacture other types of wound dressings, surgical dressings, and other medical devices. Other types of non-medical devices may also be manufactured, including shoe inner-soles. One of ordinary skill in the art will appreciate that different materials may be used for the backing film 120, the adhesive layer 80 and the second outer layer 110 to manufacture products having selected features. For example, the adhesive layer 80 may be made of hydrogel, non-woven, foam (e.g. polyurethane foam), etc.

Persons of ordinary skill in the art will appreciate that variations may be made without departure from the scope and spirit of the invention. This true scope and spirit is defined by the appended claims, interpreted in light of the foregoing.

We claim:

1. A method for manufacturing wound dressings comprising the steps of:
   providing a continuous supply of a first outer layer having a support layer and a backing layer, the support layer being of a material sufficient to protect the backing layer and having a release coating;
   providing a continuous supply of a second outer layer having a second release coating;
   providing a subject layer of a material having predetermined malleability and a first surface and a second surface;
   contouring and attaching the first outer layer to the first surface of the subject layer and attaching the second outer layer to the second surface of the subject layer, and to form a first intermediate product at a contouring and laminating station;
   removing the support layer from the backing film on the first intermediate product at a delaminating station to form a second intermediate product comprising the subject layer interposed between the backing layer and the second outer layer; and
   cutting the second intermediate product into discrete end products by carrying the second intermediate product through a cutting station in a predetermined registered and timed relationship.

2. A method as claimed in claim 1 further comprising the step of driving the second intermediate product to the cutting station using a driving station.

3. A method as claimed in claim 1 wherein the step of providing the first outer layer includes the step of attaching the support layer to the backing film.

4. A method as claimed in claim 1 wherein the backing film is made of a material selected from the group consisting of a polyethylene film, a polyurethane film, and a non-woven.

5. A method as claimed in claim 1 wherein the step of providing the first outer layer includes the step of attaching the support layer comprising a silicone release coated paper film to the backing film.

6. A method as claimed in claim 1 wherein the step of providing the first outer layer includes the step of attaching the support layer comprising a silicone release coated rubber film to the backing film.

7. A method as claimed in claim 1 wherein the subject layer is made of a material selected from the group consisting of a hydrocolloid adhesive, a hydrogel, a non-woven, a polyurethane foam, an adhesive foam and an adhesive coated foam.

8. A method for manufacturing wound dressings comprising the steps of:
   providing a continuous supply of a first outer layer having a support layer and a backing layer, the support layer being of a material sufficient to protect the backing layer and having a release coating;
   providing a continuous supply of a second outer layer having a second release coating;

providing a subject layer of a material having predetermined malleability and a first surface and a second surface;

contouring and attaching the first outer layer to the first surface of the subject layer and attaching the second outer layer to the second surface of the subject layer, and to form a first intermediate product at a contouring and laminating station, the contouring and laminating station comprising a contouring and laminating roller and a second roller, the contouring and laminating roller positioned opposite the second roller so as to drive the first intermediate product by co-operating rotational action of the contouring and laminating roller and the second roller thereby precluding the need for a driving station;

removing the support layer from the backing film on the first intermediate product at a delaminating station to form a second intermediate product comprising the subject layer interposed between the backing layer and the second outer layer; and cutting the second intermediate product into discrete end products by carrying the second intermediate product through a cutting station in a predetermined registered and timed relationship.

9. A method as claimed in claim 8 wherein the step of providing the first outer layer includes the step of attaching the support layer to the backing film.

10. A method as claimed in claim 8 wherein the step of providing the first outer layer includes the step of attaching the support layer comprising a silicone release coated paper film to the backing film.

11. A method as claimed in claim 8 wherein the step of providing the first outer layer includes the step of attaching the support layer comprising a silicone release coated rubber film to the backing film.

12. A method as claimed in claim 8 wherein the subject layer is made of a material selected from the group consisting of a hydrocolloid adhesive, a hydrogel, a non-woven, a polyurethane foam, an adhesive foam and an adhesive coated foam.

* * * * *